United States Patent [19]

Monks et al.

[11] 4,083,947
[45] Apr. 11, 1978

[54] ORGAN VISUALIZATION

[75] Inventors: Reginald Monks; Anthony Leonard Mark Riley, both of Amersham, England

[73] Assignee: The Radiochemical Centre Limited, England

[21] Appl. No.: 698,606

[22] Filed: Jun. 22, 1976

[30] Foreign Application Priority Data

Jul. 2, 1975 United Kingdom ............... 27947/75

[51] Int. Cl.$^2$ ...................... A61K 43/00; A61K 29/00
[52] U.S. Cl. ...................................... 424/1; 260/397.2; 260/397.5; 250/303; 424/9; 424/1.5
[58] Field of Search ............................... 424/1, 1.5, 9; 260/397.2; 250/303

[56] References Cited

U.S. PATENT DOCUMENTS 3,784,576   1/1974   Counsell ........................... 260/397.2
3,952,030   4/1976   Chambers et al. ............ 260/397.2 X Primary Examiner—Benjamin R. Padgett
Assistant Examiner—Christine M. Nucker
Attorney, Agent, or Firm—Wenderoth, Lind & Ponack

[57] ABSTRACT

Novel selenium derivatives of steroids have the formula I,

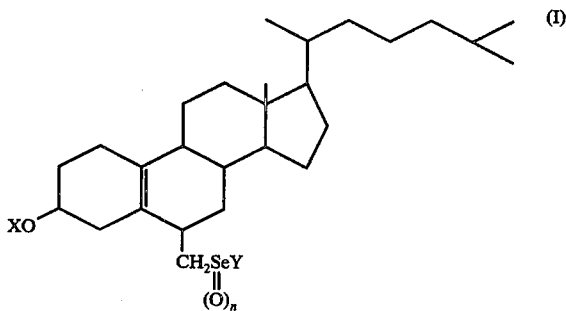

where X is hydrogen or acyl, Y is hydrocarbon and $n$ is 0 or 1, preferably 0. Such compounds, labelled with selenium-75 are of use for investigating body function, particularly for imaging the adrenal glands, and are claimed superior for the purpose to the 6$\beta$- and 19-iodine derivatives of cholesterol.

7 Claims, No Drawings

ORGAN VISUALIZATION

This invention relates to certain selenium-75 labelled steroids, and to their use in investigating body function and particularly in visualizing the adrenal glands.

There have been reports describing the preparation of radio-iodinated steroids, and the ability of certain of these compounds to concentrate in the adrenal glands has been demonstrated. When labelled with a gamma emitting isotope of iodine, such steroids may be used as agents for visualizing the adrenal glands. By way of example, 19-iodocholesterol-$^{131}$I has been shown to concentrate in the adrenal glands of rats, dogs and humans, and is now used for the visualization of human adrenal glands.

In our U.S. patent application Ser. No. 550,909, now U.S. Pat. No. 4,024,234 we sought to exploit certain advantages which steroids labelled with selenium-75 would have over their iodine-131 analogues, if they were to concentrate in human adrenal tissue. These advantages are enumerated in the above-mentioned patent and are briefly the following: the radiation dose to the patient arising from undesirable beta emission is less, a smaller dose of $^{75}$Se than of $^{131}$I suffices to give rise to a desired number of scannable photons, the energy of the $^{75}$Se gamma photons is more suitable for organ visualization, and, furthermore, the longer half-life of $^{75}$Se coupled with the greater stability of selenium-containing steroids than of iodinated steroids allows the labelled derivatives to be stored for longer periods.

However, in the case of one selenium analogue of 19-iodocholesterol, viz. 19-methylselenocholesterol, it has been shown that whereas the $^{75}$Se-labelled compound is concentrated strongly in rat adrenal tissue its uptake into the human adrenal gland is poor; some instances have been cited of its uptake into pheochromocytomas of human adrenal medullary tissue but it appears not to be concentrated in the adrenal cortex. This variation in biochemical behaviour between different animal species renders prediction of efficacious radiopharmaceutical agents a difficult matter.

Recently M Kojima and M Maeda (J. C. S. Chem. Comm., No.2, Jan. 15, 1975) have described the homoallylic rearrangement of 19-iodocholesterol to 6β-iodomethyl-19-norcholest-5(10)-en-3β-ol and have confirmed that the $^{131}$I-iodinated rearranged product is a far more effective adrenal scanning agent than 19-iodocholesterol-$^{131}$I. This present invention arises from the idea that $^{75}$Se-labelled derivatives corresponding to the above-mentioned rearranged product may be synthesized and exhibit a similarly enhanced affinity for adrenal tissue.

The present invention provides in one aspect a series of novel selenium compounds derived from cholesterol and having the general formula:

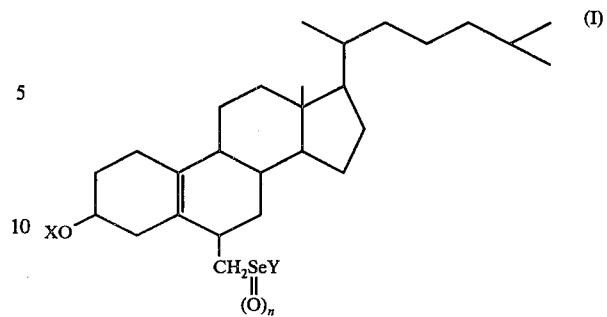

where
X is hydrogen or acyl,
Y is hydrocarbon, preferably containing up to 30 carbon atoms, and
n is 0 or 1.

This invention includes the inactive compounds, and also, more particularly, the compounds labelled with $^{75}$Se. The inactive compounds are useful aids in determining the properties of the radioactive compounds.

The present invention also provides a method of investigating body function of a mammal, which method comprises introducing into the live mammal a $^{75}$Se derivative of cholesterol as defined above, allowing the labelled steroid to become absorbed and localised in the mammal, and then observing the radiation emitted by the labelled steroid in the mammal and/or its excreta. This investigation of body function may involve visualizing a part, e.g. of the adrenal glands, of the mammal, by introducing into the live mammal a $^{75}$Se derivative of cholesterol as defined above, allowing the labelled steroid to concentrate in the part, e.g. the adrenal glands, and observing the radiation emitted by the labelled steroid in the said part. When the mammal is an adult human being, the dose administered is generally in the range 0.05 mCi to 5 mCi.

Techniques for introducing a steroid into live mammals and allowing it to become absorbed and localised, are known in the art and will not be further described here. Observation of the gamma-radiation emitted by the selenium-75, and visualization of the adrenal glands or other parts of the mammal where the labelled steroid is concentrated, can be effected with standard equipment.

The compounds may be prepared by the following steps i. effecting arrangement of a 19-halocholesterol by heating the 19-halocholesterol in an appropriate solvent, e.g. ethanol, propan-2-ol, acetic acid or acetonitrile, for a suitable length of time, e.g. several hours. the major rearrangement product is 6β-halomethyl-19-norcholest-en-3β-ol having the formula

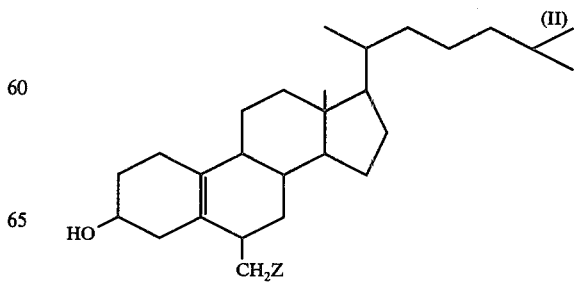

where Z = Cl Br or I. The intermediate product of this formula may also be obtained by heating 19-tosyloxy cholesterol with an alkali metal halide in an appropriate solvent for a suitable length of time, e.g. refluxing with sodium iodide in propan-2-ol for 7 hours.

ii. reacting the intermediate product so obtained with a suitable selenium compound, e.g. a sodium alkyl, cycloalkyl or aryl selenide, as more fully described below, in any convenient solvent which is unattacked by the reagents under the normal reaction conditions.

iii. if desired, acylating the 3-hydroxyl group. This can be done before or after step ii. The acylating agent may be any organic monocarboxylic acid, preferably containing up to 30 carbon atoms, for example, acetic, propionic, butyric, benzoic, oleic, linoleic or stearic acid.

iv. if desired, oxidising the seleno-steroid, e.g. by exposure to hydrogen peroxide, to give the selenoxide.

It is possible that the compounds with which this invention is concerned may have been inadvertantly made previously as minor impurities in the preparation of corresponding 19-seleno derivatives of cholesterol. If so, we believe that such impurities would never have been recovered or purified. This invention accordingly envisages the compounds defined above in admixture with from 0% to 50% by weight of (and preferably free or substantially free of) the corresponding 19-seleno derivative of cholesterol.

More particularly, the selenoalkyl group may be introduced at the 6-methyl position of 6-methyl-19-norcholest-5(10)-en-3β-ol by displacement of certain 6-methyl substituents by selenium-containing nucleophiles.

Nucleophilic Substitution at the 6-methyl Carbon Atom

Suitable leaving groups include Cl⁻, Br⁻, I⁻ and certain sulphonates (e.g. p-toluene sulphonate ion). The nucleophiles include the hydrocarbon selenide ion (YSe⁻, where Y is as hereinbefore defined) diselenide ion ($Se_2^{2-}$), hydrogen selenide ion (HSe⁻), selenocyanate ion (Se CN⁻), benzyl selenide ion

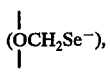

selenosulphate ion ($SeSO_3^{--}$), and pseudo-isoselenouronium ion ((NH) (NH₂)CSe⁻). The cations of these compounds are generally alkali metals, ammonium or hydrogen. The YSe⁻ ion gives the desired product directly; the others may be converted to this group in subsequent known reactions. Thus, the selenium compound chosen can determine the nature of the group Y in the final product. We envisage using a salt of an alkyl, e.g. methyl, butyl or octadecyl, selenide; a cycloalkyl, e.g. cyclohexyl, selenide; and aryl, e.g. phenyl or naphthyl, selenide; an aralkyl, e.g. benzyl, selenide; or an alkaryl, e.g. a tolyl, selenide. It would be perfectly feasable to use a compound having ethylenic unsaturation.

These reactions are similar to known reactions, and suitable conditions will be evident to those skilled in the field. However, it may be necessary to regulate the reaction conditions carefully (e.g. temperature, pH, solvent) in order to exclude or at least minimise side reactions.

EXAMPLE

where Ch is the residue of 19-nor-cholest-5(10)-en-3β-ol attached to the CH₂ group in the 6-position and Q is a leaving group,

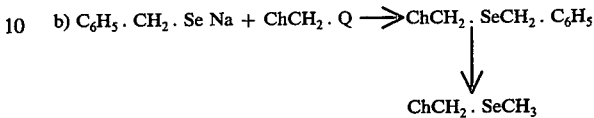

(1) sodium in liquid ammonia
(2) Methylate (e.g. CH₃I or (CH₃)₂SO₄)

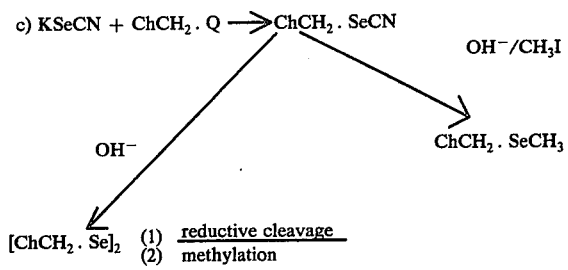

Reductive cleavage can be effected using, for example, dithiothreitol or sodium borohydride.

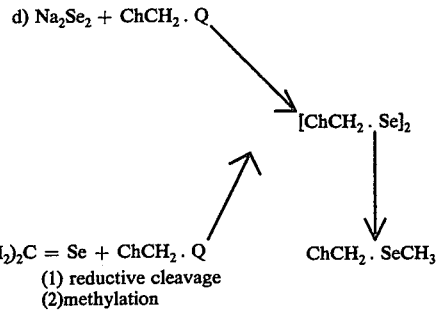

(1) reductive cleavage
(2) methylation

A wide range of solvents may be used for the above reactions. Among the more useful ones are acetone, isopropanol, and dimethylformamide.

3-Esterified and selenoxide derivatives of 6-seleno-derivative may be prepared by known methods.

When administered to rats the compounds described here have been shown to concentrate preferentially in the adrenal glands. In dogs, 6β-methylselenomethyl-19-norcholest-5(10)-en-3β-ol-⁷⁵Se concentrates in the adrenal cortex. Furthermore, 6β-methylselenomethyl-19-norcholest-5(10)-en-3β-ol-⁷⁵Se has been shown to concentrate in the adrenal glands of humans enabling their visualization and the detection of adrenal cortex adenomas.

The following Examples are illustrative of the invention.

EXAMPLE 1

Preparation of 6β-methylselenomethyl-19-norcholest-5(10)-en-3β-ol-⁷⁵Se

Sodium (12.2 mg) was added to a reaction vessel containing red selenium (42 mg; 1.8Ci) suspended in 15 ml of liquid ammonia, the reaction vessel being connected to a vacuum manifold and vented to the atmosphere via a carbosorb/charcoal trap. The reaction mixture was stirred for approximately 15 minutes until a red-brown solution of disodium diselenide was obtained. Methyl iodide (420µl of 10% v/v solution in pentane) was added to the stirred solution to give an almost colourless solution of dimethyl diselenide. A further quantity of sodium (28 mg) was added piecewise until an intense blue colouration was observed. After evaporation of the ammonia a residue of sodium methyl selenide remained. Traces of volatile materials were removed under reduced pressure.

6β-iodomethyl-19-norcholest-5(10)-en-3β-ol (70 mg) in dimethylformamide (3 ml) was added to the sodium methyl selenide under an atmosphere of nitrogen. After stirring the solution for 20 hours the dimethylformamide was removed under reduced pressure. The residue was dissolved in chloroform (10 ml) and the solution then washed with 10% aqueous sodium bicarbonate (10 ml) and water (2 × 6 ml). Evaporation of the chloroform afforded a residue of crude 6β-methylselenomethyl-19-norcholest-5(10)-en-3β-ol-$^{75}$Se which was purified by preparative layer chromatography (Merck Kieselgel 60 PF$_{254}$,1 mm; chloroform, acetone 98:2). The major component at Rf 0.4, as observed by autoradiography, was removed from the plate and extracted into ethyl acetate (3 × 3 ml). Evaporation of the ethyl acetate afforded a residue of 6β-methylselenomethyl-19-norcholest-5(10)-en-3β-ol-$^{75}$Se (198 mCi).

TLC (Merck Kieselgel 60 F254; chloroform, acetone/98:2)

Major component (greater than 95%), Rf 0.55)

I R Spectrum $\bar{\nu}_{max}$ 3400, 2930, 2870, 1470, 1385, 1200, 1160, 1085, 1050, 965 cm$^{-1}$.

EXAMPLE 2

Preparation and Analysis of 6β-methylselenomethyl-19-norcholest-5(10)-en-3β-ol

A batch of non-radioactive 6β-methylselenomethyl-19-norcholest-5(10)-en-3β-ol was prepared by the method described in Example 1. Quantities of reagents used: red selenium, 157 mg; sodium(1), 46 mg; methyl iodide, 530 µl of 33% v/v solution in pentane; sodium(2), 66 mg; 6β-iodomethyl-19-norcholest-5(10)-en-3β-ol, 300 mg. The isolation of the required product by preparative layer chromatography was aided by comparison with a radioactive marker prepared as in Example 1. Yield of 6β-methylselenomethyl-19-norcholest-5(10)-en-3β-ol, 90 mg.

TCL analysis of product on Merck Kieselgel 60 F$_{254}$

In the following eluent systems the product, visualized by phosphoric acid spray, chromatographed as a single component and coincided in Rf with the radioactive marker prepared in Example 1.
Chloroform, acetone/95:5, Rf 0.75;
Chloroform, ethanol/1:1, Rf 0.94;
Benzene, chloroform/6:4, Rf 0.14;

I R Spectrum $\bar{\nu}_{max}$ 3380, 2930, 2870, 1470, 1380, 1200, 1160, 1085, 1050, 965 cm$^{-1}$.

NMR (100 MHz, CDCl$_3$)

τ 6.04 (complex multiplet, 1, C$_3$-proton),
τ 7.25 (dd,2, J$_{gem}$ 12 cps, 3 cps, 6-CH$_2$Se-),
τ 7.52 (t,1, J$_{gem}$ 12 cps, C$_6$-proton),
τ 8.03 (S,3, Se-methyl protons),
τ 9.12 (S,6, C$_{26,27}$-protons - tentative assignment),
τ 9.18 (S,3, C$_{21}$-protons - tentative assignment),
τ 9.32 (S,3, C$_{18}$-protons - tentative assignment).

EXAMPLE 3

Preparation of 6β-butylselenomethyl-19-norcholest-5(10)-en-3β-ol-$^{75}$Se

The procedure employed in Example 1 was applied to the preparation of 6β-butylselenomethyl-19-norcholest-5(10)-en-3β-ol-$^{75}$Se. The following quantities of reagents were used:
Red Selenium, 31 mg, 326 mCi; Sodium(1) 7.6 mg; butyl iodide, 97.6 µl in 0.5 ml pentane; sodium(2), 31 mg; 6β-iodomethyl-19-norcholest-5(10)-en-3β-ol, 50 mg in 3ml of dimethylformamide.

The crude product was purified by preparative layer chromatography (Merck Kieselgel 60 PF$_{254}$,1 mm; chloroform, acetone/98:2), and the major component at Rf 0.3, as observed by autoradiography, was isolated as in Example 1 to yield 30 mCi of 6β-butylselenomethyl-19-norcholest-5(10)-en-3β-ol-$^{75}$Se.

TLC (Merck Kieselgel 60 F$_{254}$; chloroform, acetone/98:2)

Major component Rf 0.6, 85%;
Minor component Rf 0.5, 10%.

IR Spectrum $\bar{\nu}_{max}$ 3440, 2930, 2860, 1630, 1465, 965, 910 cm$^{-1}$.

EXAMPLE 4

Preparation of 6β-cyclohexylselenomethyl-19-norcholest-5(10)-en-3β-ol-$^{75}$Se

The procedure employed in Example 1 was applied to the preparation of 6β-cyclohexylselenomethyl-19-norcholest-5(10)-en-3β-ol-$^{75}$Se. The following quantities of reagents were used:
red selenium, 36 mg, 720µCi; sodium(1), 12.8 mg; cyclohexyl bromide 70µl in 0.5 ml hexane; sodium(2), 31 mg; 6β-iodomethyl-19-norcholest-5(10)-en-3β-ol, 45 mg in 3 ml of dimethylformamide.

During the second addition of sodium metal there was a colour change which progressed through orange, green, brown and colourless to blue. The crude product was purified by preparative layer chromatography (Merck Kieselgel 60 PF$_{254}$,1 mm; chloroform), and the major component at Rf 0.3, as observed by autoradiography, was isolated as in Example 1 to yield 15µCi of 6β-cyclohexylselenomethyl-19-norcholest-5(10)-en-3β-ol-$^{75}$Se.

TLC (Merck Kieselgel 60 F$_{254}$; chloroform, acetone/98:2)

Major component, Rf 0.55, 84%.

IR Spectrum $\bar{\nu}_{max}$ 3360, 2930, 2860, 1470, 1450, 1380, 1360, 1260, 1180, 1050, 960 cm$^{-1}$.

EXAMPLE 5

Preparation of
6β-benzylselenomethyl-19-norcholest-5(10)en-3β-ol-$^{75}$Se

Sodium (43 mg) was added to a reaction vessel containing red selenium (131 mg; 4 mCi) suspended in 15 ml of liquid ammonia, the reaction vessel being connected to a vacuum manifold and vented to the atmosphere via a carbosorb/charcoal trap. The reaction vessel was stirred for approximately 15 minutes until a red-brown solution of disodium diselenide was obtained.

Benzyl bromide (300μl in 700μl of hexane) was added to the stirred solution whereupon a yellow precipitate of dibenzyl diselenide formed. After evaporation of the ammonia the dibenzyl diselenide was recrystallized from ethanol/water. To the dibenzyl diselenide (88 mg) in liquid ammonia was added sodium (12 mg), which produced a colour change progressing through yellow, rose pink and red to brown. Evaporation of the ammonia yielded a residue of sodium benzyl selenide. Traces of volatile materials were removed under reduced pressure.

6β-iodomethyl-19-norcholest-5(10)-en-3β-ol (150mg) in dimethylformamide (5 ml) was added to the sodium benzyl selenide under an atmosphere of nitrogen. After stirring the solution for 20 hours the dimethylformamide was removed under reduced pressure. The residue was dissolved in chloroform (10 ml) and the solution then washed with 10% aqueous sodium bicarbonate (10 ml) and water (2 × 6 ml).

Evaporation of the chloroform afforded a residue of crude 6β-benzylselenomethyl-19-norcholest-5(10)-en-3β-ol-$^{75}$Se which was purified by preparative layer chromatography (Merck Kieselgel 60 PF$_{254}$,1 mm; chloroform). The component at Rf 0.34, as observed by autoradiography, was removed from the plate and extracted into ethanol (3 × 3 ml). Evaporation of the ethanol afforded a residue of 6β-benzylselenomethyl-19-norcholest-5(10)-en-3β-ol-$^{75}$Se (150μCi).

TLC (Merck Kieselgel 60 F$_{254}$, chloroform)

Major component (greater than 95%), Rf 0.57.

IR Spectrum $\bar{v}_{max}$ 3380, 2900, 1450, 1380, 1160, 1180, 1050, 960, 695 cm$^{-1}$.

EXAMPLE 6

Preparation of
6β-methylselenomethyl-19-norcholest-5(10)-en-3β-ol-acetate-$^{75}$Se A solution of 6β-methylselenomethyl-19-norcholest-5(10)-en-3β-ol-$^{75}$Se (1.3 mg; 11 mCi; 4.05 Ci/mmol) in dry pyridine (1 ml) and acetic anhydride (1 ml) was allowed to react at room temperature for 18 hours. Volatile components were then removed under reduced pressure. The residue was dissolved in chloroform (0.25 ml) and purified by preparative layer chromatography (Merck Kieselgel 60 PF$_{254}$; chloroform). The major component at Rf approx 0.5 was removed and extracted into ethanol to yield 11 mCi of 6β-methylselenomethyl-19-norcholest-5(10)-en-3β-ol-acetate-$^{75}$Se.

TLC (Merck Kieselgel 60 F$_{254}$; chloroform)

Major component (greater than 95%), Rf 0.73.

IR Spectrum

Showed presence of acetate groups, $\bar{v}_{max}$ 1235, 1735 cm$^{-1}$.

EXAMPLE 7

Preparation of
6β-methylselenomethyl-19-norcholest-5(10)-en-3β-ol selenoxide-$^{75}$Se To 6β-methylselenomethyl-19-norcholest-5(10)-en-3β-ol-$^{75}$Se (1.1 mg; 10 mCi) in ethanol (1 ml) was added 0.5 ml of 0.29% w/v hydrogen peroxide solution. The solution was allowed to react for 15 minutes and was then evaporated to dryness under reduced pressure. The residue of selenoxide product was dissolved in ethanol (1 ml). TLC of the product (Merck Kieselgel 60 F$_{254}$; chloroform) revealed a single component at Rf 0.0.

EXAMPLE 8

Preparation of
6β-phenylselenomethyl-19-norcholest-5(10)-en-3β-ol-$^{75}$Se

To aniline (0.1794 g; 2.16 mmol) in dilute hydrochloric acid solution (4 ml of 1 M) was added sodium nitrite (0.1514 g; 2.19 mmol) in water (1 ml), the pH of the solution then being adjusted to 5.5 by the addition of saturated sodium acetate solution. The reaction mixture was maintained at a temperature below 5° C by the addition of ice. After 30 minutes potassium selenocyanate-$^{75}$Se (16.3 mCi; 1.677 mmol) in water (10 ml) at 5° C was added. The mixture was stirred for 2½ hours and allowed to attain room temperature. It was then extracted with chloroform (2 × 10 ml) and the chloroform extract separated and dried over anhydrous sodium sulphate. After evaporation of the chloroform the residue was subjected to preparative layer chromatography (Merck Kieselgel 60 PF$_{254}$, 1 mm; hexane, methanol/19:1). The major component at Rf 0.6, as observed by autoradiography, was removed from the plate and extracted into chloroform to yield a solution of 4 mCi of phenyl selenocyanate-$^{75}$Se.

An aliquot of the chloroform solution of phenyl selenocyanate-$^{75}$Se (1.13 mCi; 0.116 mmol) was evaporated to dryness and the residue dissolved in ethanol (1 ml) plus aqueous sodium hydroxide (250μl of 0.5 M). To the solution was added dithiothreitol (20.9 mg; 0.136 mmol) in ethanol (2 ml) and then 6β-iodomethyl-19-norcholest-5(10)-en-3β-ol (10.7 mg; 0.021 mmol) in ethanol (2 ml). After remaining at room temperature for 30 minutes the reaction mixture was heated at 95° C for 2 hours and then allowed to cool. The residue remaining after evaporation of the ethanol was partitioned between chloroform (2 ml) and water (2 ml). The chloroform phase was separated and reduced in volume. Analytical TLC (Merck Kieselgel 60 F$_{254}$; chloroform) indicated a major component, Rf 0.97, and two minor componets, Rfs 0.6 and 0.7. Preparative layer chromatography (Merck Kieselgel 60 PF$_{254}$, 1 mm; chloroform) of the crude product afforded 70μCi of the component corresponding to Rf 0.6 on analytical TLC. The IR spectrum of this purified product agreed with the structure of 6β-phenylselenomethyl-19-norcholest-5(10)-en-3β-ol-$^{75}$Se.

IR Spectrum $\bar{v}_{max}$ 3430, 2930, 2860, 1640, 1580, 1470, 1385, 1260, 1200, 1160, 109–1020 (broad), 965, 800 730, 690 cm$^{-1}$.

EXAMPLE 9

Preparation of 6β-octadecylselenomethyl-19-norcholest-5(10)-en-3β-ol-$^{75}$Se

Sodium (2.4 mg) was added to a reaction vessel containing red selenium (8 mg; 2.2 mCi) suspended in 15 ml of liquid ammonia, the reaction vessel being connected to a vacuum manifold and vented to the atmosphere via a carbosorb/charcoal trap. The reaction mixture was stirred for approximately 15 minutes until a red-brown solution of disodium diselenide was obtained. Octadecyl iodide (43 mg in 0.5 ml of hexane) was added to the stirred solution, which was allowed to react for 45 minutes whilst the ammonia evaporated. Traces of volatile materials were removed from the residue of crude dioctadecyl diselenide by maintaining it under reduced pressure.

Dithiothreitol (16 mg) and aqueous sodium hydroxide (200 μl of 5 molar) in ethanol (15 ml) were added to the dioctadecyl diselenide under an atmosphere of nitrogen. After stirring the solution for 5 minutes 6β-iodomethyl-19-norcholest-5(10)-en-3β-ol (60 mg) in ethanol (5 ml) was added. The reaction mixture was then heated under reflux for 6 hours, allowed to cool, and evaporated to dryness under reduced pressure. The residue was dissolved in chloroform (6 ml) and the solution washed with 10% aqueous sodium bicarbonate (10 ml) and water (2 × 10 ml). After evaporation of the chloroform the residue was subjected to preparative layer chromatography (Merck Kieselgel 60 PF$_{254}$, 1 mm; chloroform) and the component at Rf 0.5, as observed by autoradiography, was removed from the plate and extracted into ethanol to yield 150μCi of 6β-octadecylselenomethyl-19-norcholest-5(10)-en-3β-ol-$^{75}$Se.

IR Spectrum $\bar{v}_{max}$ 2920, 2850, 1470, 1380, 1070, 1030, 695 cm$^{-1}$.

EXAMPLE 10

Preparation of 6β-methylselenomethyl-19-norcholest-5(10)-en-3β-ol-palmitate-$^{75}$Se A solution of 6β-methylselenomethyl-19-norcholest-5(10)-en-3β-ol-$^{75}$Se (1 mg; 7 mCi; 3.4 Ci/mmol) and palmitoyl chloride (250μl) in anhydrous benzene (2 ml) was allowed to react at room temperature for 18 hours. The benzene solution was washed with water (2 × 0.5 ml), saturated aqueous sodium acetate (0.5 ml), water (0.5 ml), and then evaporated to dryness under reduced pressure. The residue was dissolved in chloroform (0.25 ml) and purified by preparative layer chromatography (Merck Kieselgel 60 PF$_{254}$; chloroform). The major component at Rf 0.95 was removed and extracted into ethanol to yield 2.25 mCi of 6β-methylselenomethyl-19-norcholest-5(10)-en-3β-ol-palmitate-$^{75}$Se.

TLC (Merck Kieselgel 60 F$_{254}$; chloroform

Major component (approx. 85%), Rf 0.95.

IR Spectrum $\bar{v}_{max}$ 3440, 2920, 2850, 1740, 1640, 1465, 1375, 1245, 1175, 1040, 720 cm$^{-1}$.

EXAMPLE 11

Tissue Distribution of Selenium-75-Labelled Sterols

The tissue distribution and target to non-target concentration ratios for seven compounds were studied in male and female rats (150–180 g) of the C.F.Y. strain. Each compound (in a volume of 0.3ml) was injected via the tail vein into two male and two female rats. The animals were then housed in separate metabolism cages prior to sacrifice and dissecting on the sixth day post-injection.

| Compound of Example | Dose | % dose kg./g. in | | | | | | |
|---|---|---|---|---|---|---|---|---|
| | | Adrenals | Kidneys | Liver | Ovaries | Testes | Muscle | Blood |
| 1 | 40 μCi | 9.885 | 0.116 | 0.054 | 2.356 | 0.044 | 0.023 | 0.024 |
| 6 | 50 μCi | 12.561 | 0.108 | 0.074 | 3.232 | 0.041 | 0.022 | 0.025 |
| 7 | 40 μCi | 4.284 | 0.087 | 0.091 | 0.817 | 0.046 | 0.016 | 0.022 |
| 3 | 30 μCi | 7.563 | 0.052 | 0.096 | 2.553 | 0.023 | 0.012 | 0.009 |
| 4 | 1.5μCi | 3.609 | 0.038 | 0.148 | 2.568 | 0.034 | 0.012 | 0.026 |
| 5 | 10 μCi | 5.286 | 0.083 | 0.393 | 2.425 | 0.042 | 0.015 | 0.042 |
| 8 | 6.3μCi | 5.934 | 0.062 | 0.144 | 2.578 | 0.039 | 0.015 | 0.021 |

| Compound of Example | Dose | Concentration Ratio; Adrenals: | | | | | |
|---|---|---|---|---|---|---|---|
| | | Kidneys | Liver | Ovaries | Testes | Muscle | Blood |
| 1 | 40 μCi | 91.9 | 163.9 | 4.5 | 211.9 | 436.7 | 433.1 |
| 6 | 50 μCi | 116.0 | 161.1 | 5.7 | 166.4 | 536.3 | 469.2 |
| 7 | 40 μCi | 49.5 | 48.3 | 5.1 | 95.2 | 274 | 202 |
| 3 | 30 μCi | 144.8 | 79.0 | 4.0 | 268.3 | 809.6 | 581.9 |
| 4 | 1.5μCi | 75.1 | 24.9 | 1.6 | 89.8 | 303.1 | 137.4 |
| 5 | 10 μCi | 63.4 | 13.4 | 2.6 | 101.4 | 355.3 | 126.3 |
| 8 | 6.3 μCi | 109.1 | 40.0 | 3.62 | 171.2 | 418.9 | 285.8 |

EXAMPLE 12

250μCi of 6β-methylselenomethyl-19-norcholest-5(10)-en-3μ-ol-$^{75}$Se was intravenously injected into a female dog (13.7 kg). The dog was housed in a metabolism cage for the daily collection of urine and faeces. On the 6th day post-injection the animal was sacrificed (i.v. sodium pento-barbitone) and tissue and organ samples collected. The weighed samples were then assayed for radioactive content.

The resulting tissue distribution (expressed in terms of % dose kg/g) is tabulated below:

| Tissue | % of dose | % dose kg/g |
| --- | --- | --- |
| Adrenals | 0.622 | 7.240 |
| Ovaries | 0.303 | 1.571 |
| Liver | 3.894 | 0.143 |
| Kidneys | 0.712 | 0.175 |
| Lungs | 1.136 | 0.164 |
| Spleen | 0.528 | 0.083 |
| Blood | 5.989 | 0.066 |
| Muscle | — | 0.042 |
| Bile | — | 0.485 |
| Total Urine | 1.953 | — |
| Total Faeces | 27.691 | |

For the adrenal cortex a value of 9.925 was obtained for the % dose kg/g.

EXAMPLE 13

Two patients with Cushing Syndrome were injected intravenously with 500μCi of 6β-methylselenomethyl-19-norcholest-5(10)-en-3β-ol-$^{75}$Se formulated in normal saline stabilized with polysorbate. Repeated gamma camera scans and whole body-, urine- and blood measurements were made during a period of two weeks post injection. In one patient a maximum uptake of 17μCi in the left adrenal region was measured, the removed adrenal cortex adenoma, weight 66 g, containing 15μCi of $^{75}$Se. The other patient showed a $^{75}$Se uptake of 3μCi in each of both adrenal regions.

The $^{75}$Se uptake per gram of tissue in the adrenal adenoma was higher than that of 19-iodocholesterol-$^{131}$I as measured in five other adrenal cortex adenomas. In comparable cases with adrenal cortex adenomas or with adrenal cortex hyperplasia equally good adrenal scans were obtained with a smaller dose of the $^{75}$Se compound (7μCi/kg body weight as compared with 10-20μCi/kg of 19-iodocholesterol-$^{131}$I). Furthermore, the $^{75}$Se compound allowed scans to be taken at an earlier point of time after injection than was the case with 19-iodocholesterol-$^{131}$I (2-3 days in contrast to 6-10 days p.i.).

We claim:

1. Selenium derivatives of steroids having the general formula

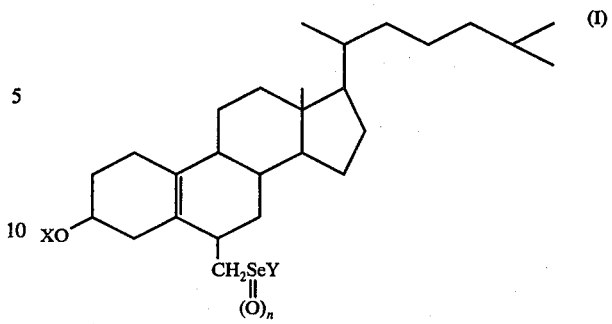

where
X is hydrogen or acyl,
Y is hydrocarbon containing up to 30 carbon atoms
n is 0 or 1.

2. Selenium derivatives of steroids as claimed in claim 1 wherein:
X is hydrogen, or C1 to C18 acyl
Y is C1 to C18 alkyl, cyclohexyl, phenyl or benzyl, and
n is 0.

3. Selenium derivatives of steroids as claimed in claim 1 wherein the selenium includes an artificially high proportion of selenium-75, rendering the compounds suitable for use as body-scanning agents.

4. A method of investigating body function of a mammal, which method comprises introducing into the live mammal a $^{75}$Se derivative of a steroid as claimed in claim 3, allowing the labelled steroid to become absorbed and localised in the mammal, and then observing the radiation emitted by the labelled steroid in the mammal.

5. A method according to claim 4 of visualizing a part of a mammal, which method comprises introducing into the live mammal a selenium derivative of a steroid as claimed in claim 3, allowing the labelled steroid to concentrate in the desired part, and observing the radiation emitted by the labelled steroid in the said part.

6. A method as claimed in claim 5, wherein the part of the mammal to be visualized is the adrenal glands.

7. A method of investigating body function of a mammal, which method comprises introducing into the live mammal a $^{75}$Se derivative of a steroid as claimed in claim 3, allowing the labelled steroid to become absorbed and localised in the mammal, and then observing the radiation emitted by the labelled steroid in the excreta of the mammal.

* * * * *